United States Patent [19]

Horin et al.

[11] 4,279,262

[45] Jul. 21, 1981

[54] HAIR TREATING AGENT OF THE PRE-SHAMPOO TYPE

[75] Inventors: Shoji Horin, Sakatashi; Shizuo Hayashi, Sugitomachi; Takeo Okumura, Sakurashi, all of Japan

[73] Assignee: Kao Soap Co., Ltd., Tokyo, Japan

[21] Appl. No.: 708,357

[22] Filed: Jul. 26, 1976

Related U.S. Application Data

[63] Continuation of Ser. No. 511,588, Oct. 3, 1974, abandoned.

[51] Int. Cl.$^3$ .................. A45D 19/00; A61K 7/06
[52] U.S. Cl. ............................. 132/7; 424/70; 424/365
[58] Field of Search .............. 5/11, 588; 424/70, 365; 132/7

[56] References Cited

U.S. PATENT DOCUMENTS

| | | | |
|---|---|---|---|
| 2,758,125 | 8/1956 | Sunde | 424/365 |
| 2,900,307 | 8/1959 | Wei | 424/365 |
| 3,052,608 | 9/1962 | Hirsh | 424/365 |
| 3,419,665 | 12/1968 | Lachampt et al. | 424/365 |
| 3,535,427 | 10/1970 | Millar et al. | 424/365 |
| 3,666,857 | 5/1972 | Russell | 424/70 X |
| 3,826,845 | 7/1974 | Suyama et al. | 424/365 |

OTHER PUBLICATIONS

Croda, Technical Data Sheet No. 1, Fluilan, Sep. 1959, pp. 1-3, and 6-10.

*Primary Examiner*—Joseph E. Evans
*Assistant Examiner*—Vera C. Clarke
*Attorney, Agent, or Firm*—Blanchard, Flynn, Thiel, Boutell & Tanis

[57] ABSTRACT

A hair treating agent of the pre-shampoo type comprising liquid lanolin emulsified in the o/w state.

7 Claims, No Drawings

HAIR TREATING AGENT OF THE PRE-SHAMPOO TYPE

This is a continuation of application Ser. No. 511,588, filed Oct. 3, 1974, now abandoned.

BACKGROUND OF THE INVENTION

1. Field of the Invention

This invention relates to a hair treating agent of the preshampoo type adapted to be coated on hair before shampooing.

2. Description of the Prior Art

Hair is contaminated with dirt and soil from external sources and with decomposition and oxidation products of sebums secreted from the scalp. Detergents used for removing such contaminants and cleaning hair, such as shampoos, usually comprise a surface active agent as the main ingredient. A shampoo containing a surface active agent alone removes indiscriminately not only the above contaminants, but also skin sebums per se which protect the hair and impart a wet toughness to hair. Hair deprived of skin sebums by shampooing lacks a wet touch or feel and if such hair is subjected to a chemical or physical cosmetic treatment such as cold waving or brushing, it is readily damaged and split or cut.

For the purpose of overcoming this disadvantage, various shampoos containing oils and fats have been proposed. Also the use of a hair rinse for imparting a wet and soft touch to hair or the application of a hair cream or hair oil after shampooing for making up for oil and fat components lost by shampooing is broadly conducted. In shampoos containing oils and fats, however, since the oil and fat components are emulsified or solubilized, most of them are removed together with the remainder of the shampoo during rinsing, and therefore, a sufficient and long-lasting effect of supplying oil and fat components to the hair cannot be attained.

A hair rinse imparts only a temporary soft touch to hair owing to the antistatic effect of a cationic surface active agent contained therein as the main active ingredient, and it scarcely exhibits an effect of making up for lost oil and fat components.

If a hair cream or hair oil is coated on hair in such a large amount that it will easily spread over all the hair, the hair becomes greasy and such greasy hair is not preferred from the cosmetic viewpoint. In contrast, if the hair cream or hair oil is coated in a small amount so that it will not impart a greasy feel to the hair, it is difficult to spread it uniformly over all the hair. Thus, overall and uniform replenishment of oil and fat components is incompatible with the desired cosmetic effect.

A hair treating method comprising coating oil and fat components on hair before shampooing and then shampooing to remove excess oil and fat components is also generally used. In this invention, the term "hair treatment of the pre-shampoo type" means a hair treating method comprising coating oil and fat components on dry hair before shampooing and washing the hair with a shampoo or the like. The oil and fat component used for this pre-treatment is called "a hair treating agent of the pre-shampoo type" in this invention.

Olive oil and camellia oil are often used as the hair treating oil and fat component of the pre-shampoo type, and creams or lotions for the hair treatment of the pre-shampoo type are commercially available. In some cases, ordinary hair creams are used for the hair treatment of the pre-shampoo type. However, in conventional hair treating agents of the pre-shampoo type, the ingredients, especially the oil and fat components, are chosen in the same manner as in general skin care cosmetics, and no specific oil and fat component for the hair treatment of the pre-shampoo type has been developed. Since hair washing is conducted after coating of a hair treating agent of the pre-shampoo type, from the cosmetic viewpoint the hair treatment using a hair treating agent of this type is preferred in comparison to the post-treatment with a hair cream or hair oil for replenishment of oil and fat after hair washing, because the hair treatment of the pre-shampoo type does not give an excessively greasy feel to hair. In this pretreatment, however, since the oil and fat component applied to hair is apt to be washed away, it is used in the non-emulsified state and hence, the effect of replenishing the oil and fat component is inferior to that attained by coating the hair with a hair cream or hair oil after shampooing. Also in the case of a conventional hair treating agent of the pre-shampoo type composed of ordinary hair cream or skin cosmetic, the effect of replenishing the oil and fat component is inferior.

SUMMARY OF THE INVENTION

The most important feature of this invention is the discovery that when liquid lanolin is emulsified in the o/w state, the penetration of the lanolin into hair is increased and is sufficient to make up for the oil and fat lost from the hair during shampooing.

Lanolin is a purified and dehydrated wax collected from wool. It melts at a temperature approximating the body temperature of man (a melting point of 36° to 42° C. as measured according to Pharmacopoeia Japonica, General Test Methods, Melting Point Measuring Method No. 2; hereinafter referred to as the "rising melting point"). Further, lanolin has excellent penetrating and moisturizing effects to the skin, and therefore, it is broadly used for the preparation of various cosmetics such as skin creams, lotions, hair creams and the like. Liquid lanolin is called dewaxed lanolin or lanolin oil, and it is prepared by removing high-melting-point waxes from lanolin. Liquid lanolin is prepared by (1) subjecting lanolin to vacuum distillation, (2) fractionally crystallizing lanolin with a solvent or (3) adding urea to lanolin to remove high-melting-point waxes. Liquid lanolin is marketed under the trademarks "Viscolan" (American Cholesterol CO.), "Fluilan" (Croda International Ltd.), "Belberan" (Nippon Lanolin Kogyo Co.) and perhaps others. The cloud points (the temperatures at which liquids become opaque when melts thereof are gradually cooled) and rising melting points of typical commercially available lanolin and liquid lanolin are shown below:

|  | Lanolin | Liquid Lanolin |
| --- | --- | --- |
| Cloud Point (°C.) | 42–46 | 17–18 |
| Rising Melting Point (°C.) | 36–40 | 3–4 |

Since liquid lanolin is a liquid fraction of lanolin separated from the higher weight solid waxy esters without chemical change, as is well known in the art, liquid lanolin has excellent penetrating and moisturizing effects to the skin in the same manner as lanolin. Further, since the viscosity of liquid lanolin is lower than that of lanolin, liquid lanolin has a better spreading property with less stickiness. Furthermore, liquid lanolin has a higher solubility in solvents such as mineral oil in comparison with lanolin, and hence, it can be easily compounded with oil and fat components of cosmetics. Accordingly, liquid lanolin is often used as a substitute for lanolin in cosmetics, in order to improve the application and feel of the cosmetics, especially their spreading property, and to reduce the stickiness of cosmetics, or because of its good adaptability to compounding. However, since the penetrating and moisturizing effects of liquid lanolin to the skin are equal to those of lanolin, even when lanolin is replaced by liquid lanolin in a cosmetic, the skin-wetting effect is not improved or no substantial improvement of this effect is attained. Further in the case of hair cosmetics which are not washed away or removed after application, such as hair creams, because the touch of the treated hair is determined by the oil and fat component sorbed to the hair, there is no substantial difference between lanolin and liquid lanolin as regards their moisturizing effect, the same as in the case of skin cosmetics. In contrast, it has been discovered that when hair is coated with a hair treating agent of the pre-shampoo type comprising, as the principal oil and fat component, liquid lanolin emulsified in the o/w state and the hair is then washed, the imparted moisturing effect is much higher in comparison with the effect attained by using a similar emulsion in which lanolin is used instead of liquid lanolin, or by using such oil and fat components as liquid lanolin, olive oil and camellia oil in the non-emulsified state. Further, the effect of emulsified liquid lanolin as the hair treating agent of the pre-shampoo type is much higher in comparison with emulsions of the oils and fats customarily used for skin creams and skin lotions, such as castor oil, beeswax, liquid paraffin and white vaseline. The mechanism whereby emulsified liquid lanolin exhibits such excellent hair treating effects has not been completely elucidated, but it is now believed that emulsified liquid lanolin has the following activities.

When emulsified liquid lanolin is coated on hair, the water constituting the continuous phase of the emulsion rapidly penetrates into the hair and it swells the hair. As this time, the emulsified liquid lanolin particles also penetrate into the hair together with the water. After the emulsion thus penetrates into the interior of hair, the excess emulsion left among the hairs or adhered on the hair surfaces is washed away during shampooing. When the washed hair is dried, the liquid lanolin, which is liquid at room temperature, acts as a plasticizer for hair keratin and softens the hair. A part of the liquid lanolin which has penetrated into the hair migrates to the surface of the washed hair to form a thin film of liquid lanolin on the surface of the hair, and it acts as a lubricating oil and reduces friction to improve the touch, combability and hairdressing adaptability of the hair. Since this surface film of liquid lanolin is very thin, it does not impart an oily and greasy feel or touch to the hair. By the combination of the foregoing effects of liquid lanolin, it is believed that a wet touch is imparted to the hair.

When the liquid lanolin in the above-described hair treating agent of the pre-shampoo type is replaced by lanolin which is not liquid at room temperature, the penetration of lanolin into the hair is much reduced. Further, since lanolin is solid at room temperature and its molecular motion is not vigorous, the effect of plasticizing keratin of washed and dried hair or the migration of lanolin onto the hair surface after drying of the hair is much reduced as compared with the case of liquid lanolin. Accordingly, it is believed that a sufficient wetting effect cannot be attained by using lanolin.

Hair is warmed in the portion very close to the scalp by body heat, but the other and a major portion of the hair is at a temperature about the same as room temperature. In contrast, the skin temperature is substantially equal to the body temperature, although it varies to some extent depending on the skin region in question. Accordingly, when emulsified lanolin is coated on the skin, since it is substantially in the molten state at that time, it will exhibit an emollient effect. Therefore, there is no substantial difference between lanolin and liquid lanolin as regards their emollient effect on the skin. This property is quite different from the property observed in the case of a hair treating agent of the pre-shampoo type.

When liquid paraffin or the like, that is liquid at room temperature, is emulsified and is used for a hair treating agent of the pre-shampoo type, since liquid paraffin is poor in its chemical or physical compatibility with hair keratin, it will not penetrate into the hair sufficiently. Further, if liquid paraffin penetrates into hair, it does not form a homogeneous solution or dispersion with keratin but exhibits a tendency to cause agglomeration of fluid paraffin (phase separation), and hence, no plasticizing effect can be attained.

When an oil and fat component having a low penetration and a low water vapor permeability, such as liquid paraffin, is coated on the skin to form a thin film on the skin surface, evaporation of water supplied to the skin from the corium is inhibited, resulting in an increase of the amount of water on the skin. Accordingly, if water evaporation is restricted appropriately, the skin is kept wet and in good condition. In the case of hair, however, water is not supplied from the interior thereof except from the hair root or the region very close to the hair root, and therefore, even if a film of an oil and fat component of a low water vapor permeability is formed on the hair surface, an effect of wetting hair cannot be obtained.

The rate of penetration of a non-emulsified oil and fat component into hair is much lower than that of water. Accordingly, in an oil and fat component is applied to hair in a non-emulsified state, the amount of the component that penetrates into the hair is much smaller than in the case of the o/w type emulsion, and hence, it is considered that a sufficient wetting effect cannot be obtained when there is employed a hair treating agent of the pre-shampoo type containing a non-emulsified oil and fat component. A similar property is observed in the case of an emulsion of the w/o type. Namely, the dispersed water particles are prevented from having a sufficient contact with the hair, and hence, such a w/o emulsion does not exhibit a sufficient swelling effect to hair.

When hair is dipped in a dehydrated oil and fat component, since the water of hydration in hair keratin migrates into the oil and fat, the diameters of the hairs decrease. When hair is dipped in water or an emulsion of the o/w type, the diameter of hair abruptly increases conspicuously. From these experimental facts, it will be understood that non-emulsified oil and fat components or emulsions of the w/o type are greatly inferior to emulsions of the o/w type with respect to their penetration into hair.

As is apparent from the foregoing description, any liquid lanolin product can be used in this invention, provided that it is liquid at room temperature (about 20°

C.), but it is preferred that a liquid lanolin product which is liquid and transparent at room temperature and which has a rising melting point lower than 10° C. is employed as the liquid lanolin according to this invention.

Suitable additional oil and fat components can be added to the o/w emulsion of liquid lanolin, depending on the desired touch and feel to be imparted to the hair when the emulsion is applied to hair (in order to attain, for example, good spreading property, good slip, refreshing feeling, heavy feeling and the like), and also various cosmetic oils and fats can be added as extenders. As such additives, there can be employed, for example, glycerides such as castor oil and olive oil, hydrocarbons such as liquid paraffin and white vaseline, alcohols such as cetyl alcohol, stearyl alcohol, oleyl alcohol and hexadecyl alcohol, and esters such as ethyl linoleate, ethyl oleate, isopropyl palmitate, decyl oleate and oleyl oleate. If the amount of such additive oils and fats is too large, the hair treating effect of the pre-shampoo type attained by the use of the o/w emulsion of liquid lanolin is reduced. Accordingly, it is critical that the amount of liquid lanolin should be at least 5% by weight, preferably at least 8% by weight, based on the total emulsion. The maximum amount of liquid lanolin is not critical, but generally it is about 40% by weight of the total emulsion.

A high-melting-point component of lanolin marketed under the designation "high-melting-point lanolin" (or the residue left after extraction of liquid lanolin from lanolin) has a sterol structure like liquid lanolin, and hence, it has a very good compatibility with liquid lanolin. When it is incorporated into liquid lanolin, it increases the melting point of liquid lanolin drastically and reduces greatly the properties of liquid lanolin required for the hair treatment of the pre-shampoo type, such as penetration into hair, hair-plasticizing effect, migration to the hair surface and the like. Accordingly, the incorporation of high-melting-point lanolin should be avoided. If incorporation of high-melting-point lanolin is needed for attaining the intended feel in the product, it is necessary to maintain the amount of high-melting-point lanolin below 10% by weight, based on the weight of liquid lanolin.

Incorporation of solid oils and fats for cosmetic use, such as solid waxes, e.g., spermaceti, beeswax, carnauba wax and montan wax, solid or semi-solid hydrocarbons, e.g., vaseline, solid paraffin, sericin and microcrystalline wax, solid fatty acids, e.g., stearic acid, and solid alcohols, e.g., cetyl alcohol and stearyl alcohol, does not have a substantial bad influence on the activity of the liquid lanolin as the hair treating ingredient of the pre-shampoo type. The reason is considered to be that because such cosmetic liquid oils and fats do not have a sterol structure, if they are homogeneously dissolved in the liquid lanolin at a high temperature in the molten state, their compatibility with liquid lanolin is reduced in hair keratin and hence, they do not inhibit the various above-described functions of liquid lanolin.

The total amount of liquid and solid cosmetic fats and oil contained with composition is from zero to 35 percent by weight, based on the total weight of the composition.

As emulsifiers to be used for emulsifying these fats and oils, there can be employed customary cosmetic emulsifiers, for example, anionic organic surfactants such as potassium, sodium and triethanolamine salts of higher fatty acids, and non-ionic organic surfactants such as glycerin higher fatty acid esters, sorbitan higher fatty acid esters, ethylene oxide adducts thereof, ethylene oxide adducts of sorbitol higher fatty acid esters, polyoxyethylene higher alcohol ethers and polyoxyethylene higher fatty acid esters. These emulsifiers can be used singly or in the form of mixtures of two or more of them. The amount of emulsifier used is an amount effective to maintain in a stable condition the o/w emulsion of liquid lanolin in water. Generally the amount of emulsifier used is from 1 to 10 percent by weight based on the total weight of the composition.

Cosmetic emulsions of the o/w type can generally be formed, provided that the aqueous phase content is higher than 25% by weight based on the total emulsion. In the hair treating agent of the pre-shampoo type, water is an indispensable component as a carrier for swelling hair and causing oil and fat particles to penetrate into the hair. Accordingly, it is critical that the water content in the emulsion should be at least 35% by weight, preferably at least 40% by weight. The maximum amount of water is not critical and it can be up to 75% by weight based on the weight of the emulsion.

The sum of the weights of liquid lanolin and water is at least 30 percent by weight, based on the total weight of the composition.

For cosmetic purposes, it is feasible to incorporate into the emulsion minor amounts of a natural moisturing agent such as amino acids or oligomers thereof, pyrrolidone carboxylic acids or potassium, sodium, ammonium, diethanolamine and triethanolamine salts thereof, and condensates of saccharides such as glucose, fructose and lipose with amino acids or oligomers thereof, a swelling agent, for example, polyhydric lower alcohols such as glycerin and propylene glycol, and a hair modifier, for example, hydrolyzates of proteins such as casein and gelatin. Further, in order to increase the cosmetic value, it is possible to incorporate conventional perfumes or dyes in the customary amounts.

The effects of the hair treating agent of the pre-shampoo type according to this invention will now be further described by reference to the following illustrative Examples.

EXAMPLE 1

Liquid lanolin (Fluilan SP manufactured by Croda International Ltd.), lanolin (Super Lanolin manufactured by Croda International Ltd.), hydrous lanolin (Lanohydrosuper manufactured by Croda International Ltd.), olive oil (reagent grade) and white vaseline (reagent grade) were separately emulsified into the o/w state by employing a mixed emulsifier of polyoxyethylene sorbitol oleate-laurate (HLB 13.2) and polyoxyethylene sorbitol hexoleate (HLB 10.2) (the mixing weight ratio of the former to the latter being 3 to 1). In each emulsion, the oil and fat concentration was 20% by weight, the emulsifier concentration was 5% by weight, and the water concentration was 75% by weight. The hair of a woman was divided into left and right portions and about 15 g each of two emulsions chosen from the above 6 emulsions were coated on the left and right portions of hair, respectively. After coating of the emulsions, the hair was washed with a commercially available shampoo and then dried. Then, the left and right portions were compared with each other with respect to their touch. Such pair comparison test was conducted with respect to each of the 6 emulsions (15 pairs total), and the test was repeated 5 times with respect to each pair. In this fashion, the wetting effect of each emulsion as a hair treatment of the pre-shampoo type was evaluated. For comparison, each emulsion was coated on the back side of a hand and the wetting effect on the skin was evaluated.

The results are shown in Table 1.

TABLE 1

| Oil and Fat Employed | Wetting Effect of Hair Treatment of Pre-Shampoo Type | Wetting Effect on Skin |
| --- | --- | --- |
| Liquid lanolin | very wet | very wet |
| Lanolin | relatively wet | very wet |
| Hydrous lanolin | relatively wet | wet |
| Olive oil | relatively wet | relatively wet |
| Cetyl alcohol | slightly wet | slightly wet |
| White Vaseline | slightly wet | slightly wet |

As is apparent from the above results, the liquid lanolin emulsion exhibited a high wetting effect if it was used as a hair treating agent of the pre-shampoo type and if it was applied to the skin. The lanolin emulsion exhibited a high wetting effect only when it was applied to the skin, but when it was used as a hair treating agent of the pre-shampoo type, the wetting effect was insufficient. The other oil and fat components were inferior to liquid lanolin with respect to both the wetting effect as a hair treatment of the pre-shampoo type and the skin-wetting effect.

EXAMPLE 2

Hairs of women were treated according to the following three methods.

(A) 25 g of an emulsion of the following composition was coated on the hair:

| | |
| --- | --- |
| Liquid lanolin (Viscolan manufactured by American Cholesterol Co.) | 20% by weight |
| Polyoxyethylene (n=5) lanolyl alcohol ether (Solulan 5 manufactured by American Cholesterol Co.) | 7% by weight |
| Triethanolamine stearate | 3% by weight |
| Water | 70% by weight |

After no minutes had passed from the coating, the hair was washed with a shampoo having the following composition:

| | |
| --- | --- |
| Triethanolamine lauryl sulfate | 16% by weight |
| Coconut oil fatty acid diethanolamide | 15% by weight |
| Water | 69% by weight |

Then, the hair was set by using a hair drier.

(B) 25 g of liquid lanolin (Viscolan) was coated on hair, and after 10 minutes had passed from the coating, the hair was washed with the same shampoo as used in the treatment (A) and then was set by a hair drier.

Each of the above treatments was conducted on 4 women, and the effects were compared. The results are shown in Table 2.

TABLE 2

| Hair Treatment | Hair Condition After Treatment |
| --- | --- |
| (A) | Very wet |
| (B) | slightly wet |

EXAMPLE 3

About 30 g of an emulsion as described in the following Table 3 was coated on the hair of a woman, and after 5 minutes had passed following the coating, the hair was washed with a commercially available shampoo and then dried. The condition of the dried hair was examined. This test was conducted on 6 women with respect to each of 6 emulsions shown in Table 3.

The results are shown in Table 3.

TABLE 3

| Emulsion | Composition (% by weight) | | | | | |
| --- | --- | --- | --- | --- | --- | --- |
| Liquid lanolin[1] | 15 | 6 | 2 | 15 | 15 | 2 |
| Liquid paraffin[2] | 9 | 18 | 22 | — | — | 14 |
| Isopropyl myristate | — | — | — | 9 | — | 5 |
| Hexadecyl alcohol | — | — | — | — | 9 | 3 |
| Emulsifier[3] | 5 | 5 | 5 | 5 | 5 | 5 |
| Glycerin | 5 | 5 | 5 | 5 | 5 | 5 |
| Macromolecular thickener[4] | 0.2 | 0.2 | 0.2 | 0.2 | 0.2 | 0.2 |
| Purified Water | 65.8 | 65.8 | 65.8 | 65.8 | 65.8 | 65.8 |
| Hair Condition After Drying | very wet | wet | ordinary | very wet | very wet | ordinary |

[1] Belberan manufactured by Nippon Lanolin Kogyo Co.
[2] 40 centistokes (37° C.)
[3] Mixture of 3 parts of polyoxyethylene sorbitan mono-oleate (HLB 15.0) and 2 parts of sorbitan mono-oleate (HLB 4.3)
[4] Carbopol 940 manufactured by Goodrich Chemical Co.

As is apparent from the above results, the wet touch or feel was reduced by decreasing the amount of liquid lanolin contained in the emulsion, and no substantial improved effect was attained when the amount of liquid lanolin was 2% by weight.

EXAMPLE 4

Blind comparison tests were conducted on 50 women by employing as hair treating agents of the pre-shampoo type, an emulsion of the following composition and an emulsion in which the liquid lanolin of the foregoing emulsion was replaced by the same amount of lanolin (Super Lanolin manufactured by Croda International Ltd.):

| | |
| --- | --- |
| Liquid lanolin (Pluilan SP manufactured by Croda International Ltd.) | 20.0% by weight |
| Liquid paraffin (40 centistokes at 37.8° C.) | 10.0% by weight |
| Isopropyl myristate | 8.0% by weight |
| Cetyl Alcohol | 2.0% by weight |
| Sorbitan monostearate (HLB = 4.7) | 2.0% by weight |
| Polyoxyethylene sorbitan monostearate (HLB = 14.9) | 3.0% by weight |
| Propyl p-hydroxybenzoate | 0.15% by weight |
| Glycerin | 7.0% by weight |
| Perfume | 0.2% by weight |
| Purified water | 47.5% by weight |

After washing and drying, the women were asked which of the two emulsions gave a better wetting effect. The results are shown in Table 4.

TABLE 4

| Answer | Number of Answers |
| --- | --- |
| Liquid lanolin-containing emulsion gave much wetter touch | 18 |
| Liquid lanolin-containing emulsion gave wetter touch | 19 |
| No difference | 9 |
| Lanolin-containing emulsion gave wetter touch | 3 |
| Lanolin-containing emulsion gave much wetter touch | 1 |

| Answer | Number of Answers |
|---|---|
| Total | 50 |

As is apparent from the above test results, the wetting effect of the liquid lanolin-containing emulsion was much higher than that of the lanolin-containing emulsion.

The embodiments of the invention in which an exclusive property or privilege is claimed are defined as follows:

1. A method of treating human hair which comprises applying to dry human hair an effective amount of the oil-in-water emulsion consisting essentially of
    from 35 to 75 percent by weight of water, as the continuous phase,
    from 5 to 40 percent by weight of liquid lanolin, as the discontinuous phase, said liquid lanolin being liquid at about 20° C.,
    from one to 10 percent by weight of a cosmetic emulsifier selected from the group consisting of anionic organic surfactants, nonionic organic surfactants and mixtures thereof, effective to maintain in a stable condition the oil-in-water emulsion of said liquid lanolin in the water,
    so as to coat the hair substantially uniformly with said emulsion whereby said liquid lanolin penetrates into the hair, and
    then shampooing and drying the hair.

2. An oil-in-water emulsion for treating hair prior to shampooing, consisting essentially of
    from 35 to 75 percent by weight of water, as the continuous phase,
    from 8 to 40 percent by weight of liquid lanolin, as the discontinuous phase, said liquid lanolin being liquid at about 20° C.,
    from one to 10 percent by weight of a nonionic organic surfactant cosmetic emulsifier or mixture of said emulsifiers effective to maintain in a stable condition the oil-in-water emulsion of said liquid lanolin in the water.

3. The oil-in-water emulsion as claimed in claim 2, also containing from zero to 35 percent by weight of compatible cosmetic fats and oils effective to improve the spreading property, slip property or feel of the emulsion on the hair.

4. An oil-in-water emulsion as claimed in claim 2 in which said nonionic organic surfactant is selected from the group consisting of glycerin higher fatty acid esters, sorbitan fatty acid esters, ethylene oxide adducts of sorbitan fatty acid esters, ethylene oxide adducts of sorbitol higher fatty acid esters, polyoxyethylene higher alcohol ethers, polyoxyethylene higher acid esters and mixtures thereof.

5. The oil-in-water emulsion as claimed in claim 2 in which said emulsifier is a mixture of (a) polyoxyethylene sorbitol oleatelaurate having an HLB value of 13.2 and (b) polyoxyethylene sorbitol hexaoleate having an HLB value of 10.2.

6. The oil-in-water emulsion as claimed in claim 2 in which said emulsifier is a mixture of polyoxyethylene sorbitan mono-oleate having an HLB value of 15 and sorbitan mono-oleate having an HLB value of 4.3.

7. The oil-in-water emulsion as claimed in claim 2 in which said emulsifier is a mixture of polyoxyethylene sorbitan monostearate having an HLB value of 14.9 and sorbitan monostearate having an HLB value of 4.7.

* * * * *